US010489035B2

(12) United States Patent
Sunna

(10) Patent No.: US 10,489,035 B2
(45) Date of Patent: Nov. 26, 2019

(54) SYSTEM WITH BREATHING APPARATUS AND TOUCH SCREEN

(71) Applicant: MAQUET CRITICAL CARE AB, Solna (SE)

(72) Inventor: Anette Sunna, Stockholm (SE)

(73) Assignee: MAQUET CRITICAL CARE AB, Solna (SE)

( * ) Notice: Subject to any disclaimer, the term of this patent is extended or adjusted under 35 U.S.C. 154(b) by 0 days.

(21) Appl. No.: 14/404,993

(22) PCT Filed: Mar. 8, 2013

(86) PCT No.: PCT/EP2013/054758
§ 371 (c)(1),
(2) Date: Dec. 2, 2014

(87) PCT Pub. No.: WO2013/182326
PCT Pub. Date: Dec. 12, 2013

(65) Prior Publication Data
US 2015/0193585 A1    Jul. 9, 2015

(30) Foreign Application Priority Data

Jun. 3, 2012 (WO) ................. PCT/EP2012/060454
Jun. 20, 2012 (WO) ................. PCT/EP2012/061901
Mar. 1, 2013 (WO) ................. PCT/EP2013/054180

(51) Int. Cl.
*G06F 3/0484* (2013.01)
*G06F 3/0488* (2013.01)
(Continued)

(52) U.S. Cl.
CPC ..... *G06F 3/04847* (2013.01); *A61M 16/0051* (2013.01); *A61M 16/021* (2017.08);
(Continued)

(58) Field of Classification Search
CPC ............ G06F 19/3406; G06F 3/04847; G06F 3/04883; G06F 19/3481; A61M 16/00
(Continued)

(56) References Cited

U.S. PATENT DOCUMENTS 5,247,434 A    9/1993  Peterson et al.
6,463,930 B2  10/2002  Biondi et al.
(Continued)

FOREIGN PATENT DOCUMENTS

CN    101561745 A    10/2009
CN    101819610 A     9/2010
(Continued)

OTHER PUBLICATIONS

Soft Button | Article about Soft button by the Free Dictionary, at http://encyclopedia2.thefreedictionary.com/Soft +button (downloaded May 8, 2017).
(Continued)

*Primary Examiner* — Mark W Regn
(74) *Attorney, Agent, or Firm* — Wesley Scott Ashton

(57) ABSTRACT

A system includes a breathing apparatus, a touch screen unit and a processing unit. A first content is displayed at a first screen location of the touch screen. Upon a user input, comprising a gesture of one or more gestures, at the first screen location, a second content related to the first content is selected and displayed in dependence of the gesture and the first content. The first content (30) is free of an indication of the second content, such as an indication comprised in the list of an icon, soft-button or a menu configured to activate the second content upon user selection on the touch screen.

24 Claims, 13 Drawing Sheets

(51) Int. Cl.
*A61M 16/00* (2006.01)
*G16H 40/63* (2018.01)
*G06F 19/00* (2018.01)
*A61M 16/10* (2006.01)

(52) U.S. Cl.
CPC ......... *G06F 3/04883* (2013.01); *G16H 40/63* (2018.01); *A61M 16/1015* (2014.02); *A61M 2205/15* (2013.01); *A61M 2205/505* (2013.01); *A61M 2205/583* (2013.01); *G06F 19/3481* (2013.01)

(58) Field of Classification Search
USPC ........................................................ 345/173
See application file for complete search history.

(56) References Cited

U.S. PATENT DOCUMENTS

| | | | |
|---|---|---|---|
| 7,225,809 | B1 | 6/2007 | Bowen et al. |
| 2002/0133061 | A1 | 9/2002 | Manetta |
| 2005/0246643 | A1 | 11/2005 | Gusmorino et al. |
| 2007/0186186 | A1 | 8/2007 | Both et al. |
| 2008/0072896 | A1* | 3/2008 | Setzer .................. A61M 16/00 128/200.24 |
| 2008/0077072 | A1 | 3/2008 | Keenan et al. |
| 2008/0077073 | A1 | 3/2008 | Keenan et al. |
| 2008/0084400 | A1* | 4/2008 | Rosenberg ............ G06F 1/1626 345/173 |
| 2008/0307353 | A1 | 12/2008 | Molducci et al. |
| 2009/0024008 | A1 | 1/2009 | Brunner et al. |
| 2009/0164944 | A1 | 6/2009 | Webster et al. |
| 2010/0138781 | A1 | 6/2010 | Korhonen et al. |
| 2010/0146459 | A1* | 6/2010 | Repka .................. G06F 3/0488 715/863 |
| 2011/0138275 | A1* | 6/2011 | Yu ....................... G06F 3/04817 715/702 |
| 2011/0167382 | A1 | 7/2011 | van Os |
| 2011/0249006 | A1 | 10/2011 | Wallace et al. |
| 2011/0315711 | A1* | 12/2011 | Hecht ..................... A47J 31/52 222/129.1 |
| 2012/0030619 | A1* | 2/2012 | Lee ....................... G06F 3/0482 715/810 |
| 2012/0212420 | A1 | 8/2012 | Shin |
| 2013/0050135 | A1* | 2/2013 | Stewart ............... G06F 3/04895 345/174 |
| 2013/0055160 | A1* | 2/2013 | Yamada ............. G06F 3/04883 715/810 |
| 2013/0222265 | A1* | 8/2013 | Smith ................. G06F 3/04883 345/173 |

FOREIGN PATENT DOCUMENTS

| | | |
|---|---|---|
| JP | H08147004 A | 6/1996 |
| JP | H09297609 A | 11/1997 |
| JP | 2000300516 A | 10/2000 |
| JP | 2001084074 A | 3/2001 |
| JP | 2001315179 A | 11/2001 |
| JP | 2007226406 A | 9/2007 |
| JP | 2010176174 A | 8/2010 |
| WO | WO-98/41267 A1 | 9/1998 |
| WO | WO-2006/074251 A2 | 7/2006 |
| WO | WO-2011/139194 A1 | 11/2011 |

OTHER PUBLICATIONS

User Guide Pantech Flex, Pantech, 2012.

* cited by examiner

SYSTEM WITH BREATHING APPARATUS AND TOUCH SCREEN

BACKGROUND OF THE INVENTION

Field of the Invention

This disclosure pertains in general to the field of breathing systems for ventilating patients having a display for providing graphical user interfaces (GUI's). More particularly, the disclosure relates to breathing systems including a breathing apparatus and a touch screen with said GUI for interaction of a user with said breathing apparatus.

Description of Background Art

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Conventional breathing apparatus like Servo Ventilator 300 of Siemens-Elema introduced during the 1990es had a large number of rotary knobs for operating the apparatus. Each of the knobs had a dedicated function and thus the apparatus had a limited number of possibilities for adjusting operation of the apparatus. At the beginning of the $21^{st}$ century, touch screens were introduced for some breathing apparatus. However, these apparatuses still had knobs, buttons or wheels with a direct access to certain functions and for adjustments of the apparatuses' operation. Over time, the number of functions and possible adjustments has increased and the number of knobs has been reduced, in some cases knobs have been completely removed from breathing apparatuses available today.

However, having removed hardware adjustment elements like knobs, wheels etc, such breathing apparatuses are lacking direct access to certain functions, which is desired in a clinical operation. Moreover, known breathing apparatuses comprising touch screens have rather complicated GUIs that may be improved. Such GUIs comprise for instance complicated menu structures through which an operator has to navigate. Menu structures are by nature limited to pre-programmed choices. This may be complicated for users of such breathing apparatus, who are not familiar with the menus and what submenus are hidden in-depth. In a clinical environment there is a need for a quick and safe user interaction with breathing apparatuses. A quick access to relevant and desired adjustments would be advantageous avoiding difficulties of a clinical user to find the adjustments in the GUI.

SUMMARY OF THE INVENTION

Accordingly, embodiments of the present disclosure preferably seek to mitigate, alleviate or eliminate one or more deficiencies, disadvantages or issues in the art, such as the above-identified, singly or in any combination by providing systems, methods, etc., according to the appended patent claims.

According to an aspect of the disclosure, a system is provided. The system includes a breathing apparatus, a display unit and a processing unit that is operatively connected to the display unit.

The display unit of the system is a touch screen for interaction of a user with the breathing apparatus. The processing unit is configured to display at least a first content at a first screen location of the touch screen. In addition, the processing unit is configured to receive a user input comprising a gesture of one or more gestures at the first screen location. Moreover, the processing unit is configured to select a second content related to the first content in dependence of the gesture and the first content. Furthermore, the processing unit is configured to provide the second content on the touch screen at a screen location at least partly including the first screen location. The first content is free of an indication of the second content, such as an indication comprised in the list of an icon, soft-button or a menu configured to activate the second content upon user selection on the touch screen. An icon has a boarder or a frame and a symbol within the border or frame delimitation, the symbol identifying a certain function to be obtained when pressing the icon. The operator has to "read" the icon. In particular if a larger number of icons is presented on a limited screen area, the same issues arise as with menu structures, namely that the operator may easily be confused in a clinical environment. Such confusion may lead to errors in operating breathing apparatus in particular circumstances, which is undesired.

In contrast, a symbol without a boarder may be presented at a first screen location and a gesture may be made on a screen location at or adjacent the symbol or a related content, like a curve. The need to identify and hit an icon for a desired operation is thus dispensed with.

In this manner, instead of a complicated menu structure, a quick and safe access to desired adjustments or specific additional information is provided.

Some examples of the disclosure may provide for faster navigation from one view to another.

A direct access is provided to non-displayed content related to displayed content without any difficulties for a user, which is in particular advantageous in many clinical situations where the user needs to focus on the patient. The non-displayed content relates to content that will be displayed as the second content, but is not displayed or accessible for the user when the first content is displayed.

An example is to switch from a screen view having no or a few ventilation parameters displayed as metrics and/or curves to another screen view having more metrics and/or curves than the first screen view. This is in detail described in PCT/EP2012/061901 of the same applicant as the present application, and which is incorporated herein in its entirety for all purposes. In particular, reference is made to claim 11 and related description passages and figures of PCT/EP2012/061901. Thus an easier and friendlier user-interface and/or faster navigation from one view to another is achieved.

Moreover, access to operational and/or patient safety is increased. The breathing apparatus is safely controlled by the clinical operator. For instance, safety critical adjustments may in an example only be accessible upon a specific gesture, such as a tap and hold for a certain time exceeding a safety threshold time. In addition, a further confirmation by the operator may be required to access certain functions of the breathing apparatus.

The user intuitively obtains a correct and desired reaction related to the first content upon input of the operator.

Some examples of the disclosure provide for a simpler, easier to use and more user-friendly user interface.

Some examples of the disclosure provide for that an optimal amount of information may be displayed as no display area is wasted for menus, soft buttons etc. at the first content.

Some examples of the disclosure also provide for that functions critical to the safety cannot easily be activated by mistake. Thus, some embodiments may provide for improved safety of the system.

In some examples of the disclosure the gesture is a tap and hold gesture, and wherein the processing unit is configured to provide the second content upon a hold time portion of the tap and hold gesture exceeding a threshold of pre-defined time length.

Furthermore, unintentional adjustments of the breathing apparatus are avoided as a specific gesture, such as a tap and hold for a certain time, is required for entering certain modes for adjustment etc. Unintentional adjustments by accidently touching the touch screen may be prevented. Such accidental touching of a touch screen may occur in a clinical environment and has thus no dire consequences by undesired or unintentional adjustments of the breathing apparatus operational parameters.

In addition, soft buttons are avoided. Soft buttons comprise a text message on the button to identify a function to be performed upon pressing the soft button on a touch screen. However, the operator has to read the text on the button and identify what action would be performed upon pressing the button. This has similar disadvantages as a menu structure mentioned in the background section. Thus, the disclosure provides for a less confusing GUI, which is a clinical advantage.

In some examples of the disclosure the processing unit is configured to provide the second content upon confirmation to display the second content by the user. Thanks to the activate confirmation of displaying the second content requiring user confirmation, the operational safety is further increased.

In some examples of the disclosure the threshold time length of the hold portion of the tap and hold gesture is dependent on the first content. In this manner, operational safety can be further increased. Screen portions with a first content requiring or leading to more critical operational adjustments than other screen areas with other content that is less critical, may require a longer time to enter the adjustments. Accidental adjustments are thus even more difficult for screen area(s) displaying such a first content.

In some examples of the disclosure the processing unit is configured to provide a visual feedback to the user during the hold portion illustrating elapsed hold time and time until the threshold is reached.

In some examples of the disclosure the processing unit is configured to provide user access to safety critical functions when the threshold is exceeded.

In some examples of the disclosure an area adjacent the touch screen is free of buttons that are associated with the first content, and/or wherein the at least the first screen location lacks one or more soft-buttons.

In some examples of the disclosure the gesture is a tap gesture.

In some examples of the disclosure the first content is included in the non-exhaustive list of
  a ventilation strategy indicator;
  a curve of a ventilation parameter;
  a metric of a ventilation parameter in normal operation;
  a metric of a ventilation parameter when an alarm limit thereof is passed;
  an O2 flush function indicator (100% O2);
  an O2 boost function indicator (adjustable O2%); or
  a control indicator for safety critical functions of the breathing apparatus, such as for stopping an on-going ventilation: and/or
  a symbol, such as a bubbles symbol, e.g. related to leakage compensation.

In some examples of the disclosure the second content is included in the list of:
  a graphical interface for adjusting operative parameters of the breathing apparatus, such as ventilation parameters, curves of ventilation parameters, or breathing modes;
  short trend curves for at least one ventilation parameter;
  an adjustment mode for scales, layout etc.
  a graphical interface for adjustment of alarm limits;
  at least one graphical loops of one or more ventilation parameters;
  a graphical interface for modification of at least one operational parameter of the breathing apparatus including at least two display areas for user modification of the operational parameter in different user interaction modes for each display area;
  a graphic illustrating a specific function of a breathing apparatus, such as graphics illustrating a leakage compensation of a breathing circuit;
  a help text and/or illustration; and/or
  a help text and/or definition of curve forms.

A graphical interface for modification of at least one operational parameter of the breathing apparatus including at least two display areas for user modification of the operational parameter in different user interaction modes for each display area is in detail described in PCT/EP2012/060454 of the same applicant as the present application, and which is incorporated herein in its entirety for all purposes.

In some examples of the disclosure the gesture, the first content and the second content are included in the non-exhaustive list of:
  a tap, a metric or curve during an alarm, alarm adjustments; and
  a tap and hold, a curve, a configuration mode for the curve.

According to another aspect of the disclosure, a method of internally controlling a breathing apparatus is disclosed. A touch screen for interaction of a user with the breathing apparatus is controlled for displaying at least a first content at a first screen location of the touch screen. Further, the method includes receiving a user input comprising a gesture of one or more gestures at the first screen location. The method includes selecting a second content, different from the first content and different for each gesture, in dependence of the gesture and the first content. Moreover, the method includes providing the second content on the touch screen.

In some examples of the disclosure the gesture is a tap and hold gesture, and providing the second content upon a hold time portion of the tap and hold gesture exceeding a threshold of pre-defined time length, and optionally providing a visual feedback to the user during the hold portion illustrating elapsed hold time and time until the threshold is reached, and wherein the threshold preferably is dependent on the first content.

In some examples of the disclosure the method includes providing user access to safety critical functions when the threshold is exceeded.

According to yet another aspect of the disclosure, a computer-readable medium having embodied thereon a computer program is disclosed for processing by one or more processing units, in particular a processing unit of a breathing system. The computer-readable storage medium has for this purpose instructions stored thereon that when executed by the processing unit perform operations for providing user communication via a touch screen of the breathing system including a breathing apparatus. The instructions include displaying at least a first content at a first screen location of the touch screen; detecting a user input comprising a gesture of one or more gestures at the first screen location; selecting a second content, different from the first content and different for each gesture, in dependence of the gesture and the first content; and providing the second content on the touch screen.

Further embodiments of the invention are defined in the dependent claims, wherein features for the second and subsequent aspects of the invention are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

DESCRIPTION OF THE PREFERRED EMBODIMENTS

Figure 1:
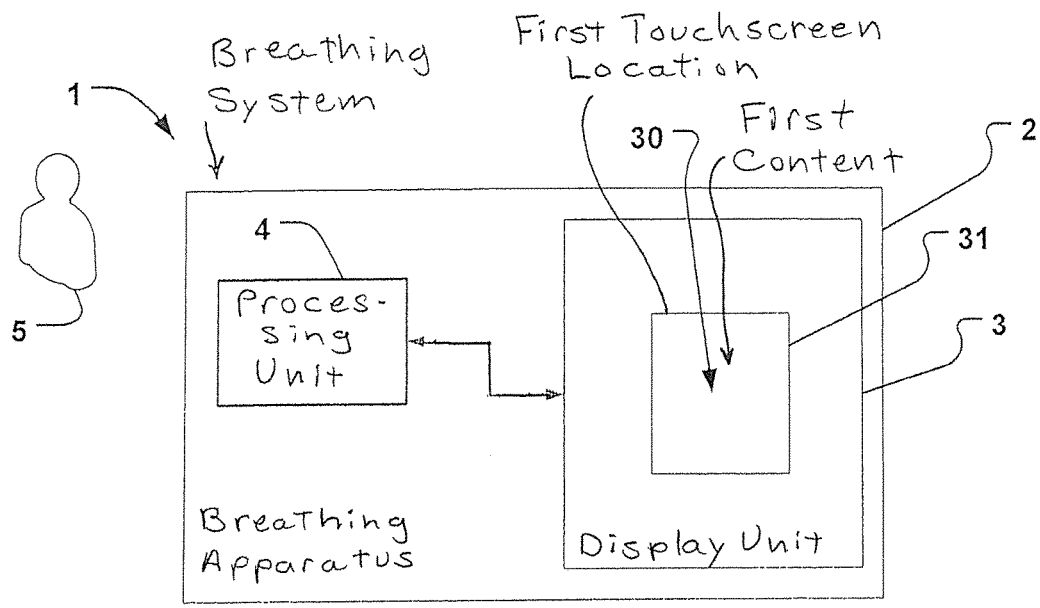
FIG. 1 is a schematic illustration of an exemplary breathing system.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The disclosure provides examples for methods and systems in which the operator intuitively reaches a related content to what is shown on selected screen areas. The content on the screen controls what types of specific user input, i.e. gestures, are accepted at for specific content of a GUI. The exact screen area where the specific content is displayed is not relevant; it is the content that controls the possible action in dependence of a gesture made by the operator of the breathing apparatus on the screen area where the specific content is displayed.

Screen area needs not be exact, like in a pre-defined framed area, but is a screen area at or adjacent a first context. Thus the disclosure provides for more tolerant user input by providing the user with a desired action without the need for searching specific buttons, but rather a specific first context to be touched with a specific gesture to obtain access to a desired second context related to the first context.

FIG. 1 is a schematic illustration of an exemplary breathing system 1. The system 1 includes a breathing apparatus 2, a display unit 3 and a processing unit 4 that is operatively connected to the display unit.

The display unit 3 of the system includes a touch screen for interaction of a user 5 with the breathing apparatus 1. The processing unit 4 is configured to display at least a first content 30 at a first screen location 31 of the touch screen. In addition, the processing unit is configured to receive a user input comprising a gesture 35 of one or more gestures at the first screen location 31.

Moreover, the processing unit 4 is configured to select a second content 40 related to the first content in dependence of the gesture and the first content 30. In this manner, the breathing apparatus is safely controlled by the clinical operator. For instance, safety critical adjustments may in an example only be accessible upon a specific gesture, such as a tap and hold for a certain time exceeding a safety threshold time. In addition, a further confirmation by the operator may be required to access certain functions of the breathing apparatus.

Furthermore, the processing unit 4 is configured to provide the second content 40 on the touch screen preferably at a screen location at least partly including the first screen location 31.

The first content 30 is free of an indication of the second content 40, such as an indication comprised in the list of an icon, soft-button or a menu configured to activate the second content upon user selection on the touch screen.

Figure 2:
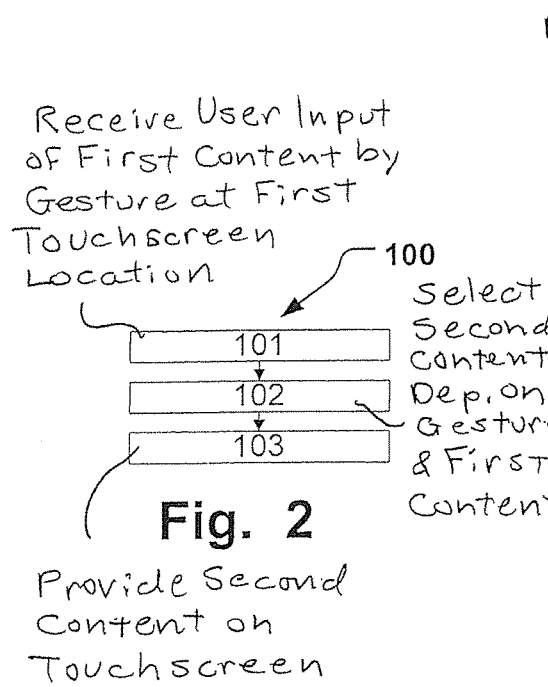
FIG. 2 is a flow chart illustrating an example of a method.

FIG. 2 is a flow chart illustrating an example of a method 100 of internally controlling a breathing apparatus 1. A display unit 3 including a touch screen for interaction of a user 5 with the breathing apparatus 1 is controlled for displaying at least a first content 30 at a first screen location 31 of the touch screen. Further, the method includes a step of receiving 101 a user input on the touch screen. The user input is performed by the user touching the touch screen and includes a gesture 35 of one or more gestures at the first screen location 31. The method 100 includes selecting 102 a second content 40, different from the first content 30 and different for each gesture 35, in dependence of the gesture 35 and the first content 30. Moreover, the method includes providing 103 the second content 40 on the touch screen.

Figure 4A:
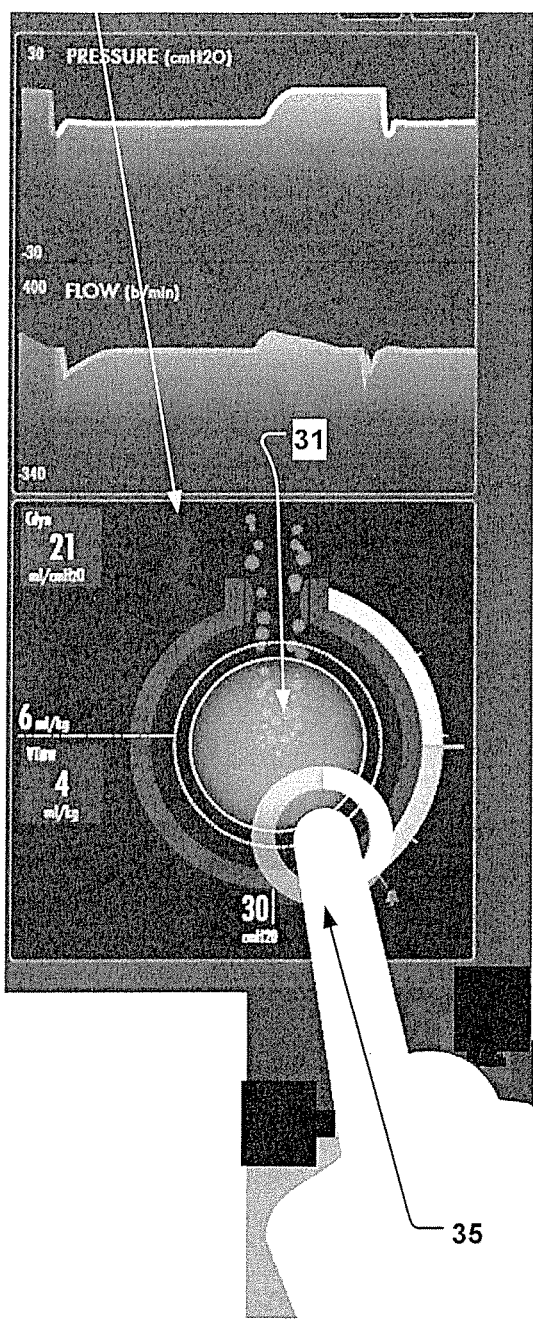
FIGS. 4A, 4B, 5A, 5B, 6A, 6B, 7A, 7B, 8A, 8B, 9A, 9B, 10A, 10B, 11A, and 11B are schematic illustrations of various examples of portions of GUIs of a display of a breathing system with a first content and a second content upon user interaction including a gesture on said first content, respectively.
Figure 4B:
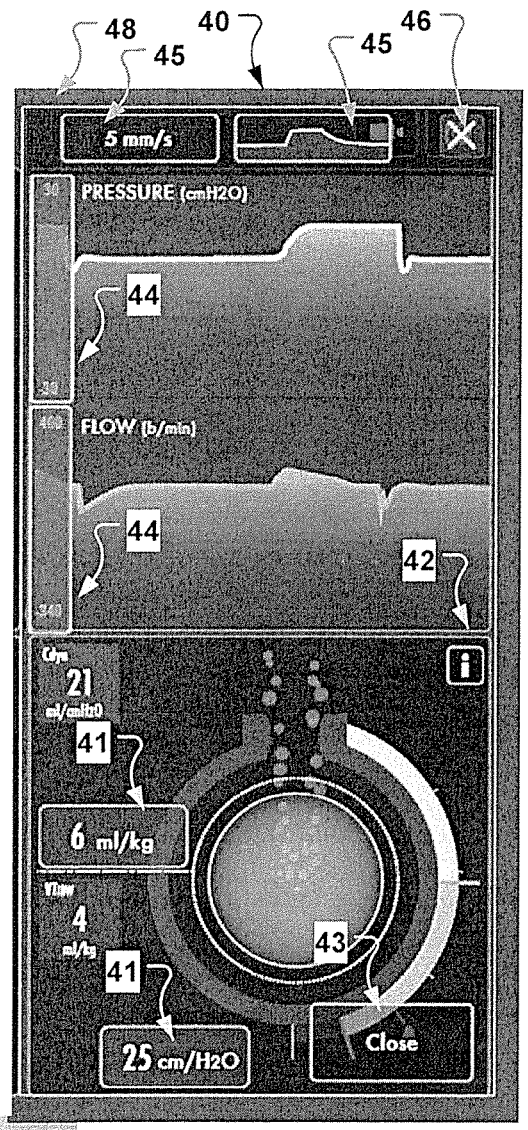

In FIG. 4A and FIG. 4B a graphical visualization of a ventilation strategy indicator is illustrated at the first screen area 31. In FIG. 4A, a first content is illustrated together with a schematically illustrated user input including a gesture 35 of an operator.

As mentioned above, it is the first content that controls the possible action in dependence of a gesture made by the operator of the breathing apparatus on the screen area where the specific first content is displayed. The input leads the operator intuitively to the correct desired second content. Moreover, the exact screen position where to touch is not critical; it is rather the first screen area 31 at the first context 30 that may be touched anywhere at the context, or even adjacent to it. For instance the strategy indicator needs not to be hit in the middle thereof by the operator's finger, as illustrated in FIG. 4A. Thus the disclosure provides for a tolerant user input by providing the user with a desired action without the need for searching specific buttons, but rather a specific first context to be touched with a specific gesture to obtain access to a desired second context related to the first context.

Here, the second context provided via a tap and hold gesture of a predetermined hold portion time is illustrated in the example as an edit mode, as illustrated in FIG. 4B.

The gesture may be a different gesture leading to a different second content. For instance a simple tap may lead to a different second content, such as a help window or similar.

Another example is a tap and hold of a hold time below the threshold time that may lead to an information window for the tap and hold gesture, or similar. Upon a simple tap, no action may be taken or a help text may be displayed that a tap and hold is necessary to access a second content. Also, the time length of the hold portion of the tap and hold gesture may be associated with different second content for different time lengths. With increasing time length for instance more critical adjustment modes may be entered. An example of such a staggered dependence of the second content to the time length would be a help menu, and edit mode for screen layout adjustments, an alarm limit adjustment mode, etc.

The ventilation strategy indicator of the example includes a combination of a target indication for at least one ventilation related parameter of a ventilation strategy for a patient ventilated by the breathing apparatus 2, and a reciprocating animation of the at least one ventilation related parameter relative the target indication. This kind of ventilation strategy indicator is described in detail in PCT/EP2013/053073 of the same applicant as the present application, and which is incorporated herein in its entirety for all purposes.

In the example illustrated in FIG. 4A, amongst others, of the disclosure the gesture 35 is a tap and hold gesture. The second content 40 is provided, as illustrated in FIG. 4B. The tap and hold gesture starts with user 5 touching the touch screen at the first screen location. The user maintains contact with the touch screen surface at substantially the same location for a hold time portion of the tap and hold gesture. The hold time has to exceed a threshold time of pre-defined time length, i.e. the user has to keep the contact before releasing the contact with the touch screen.

Figure 4C:
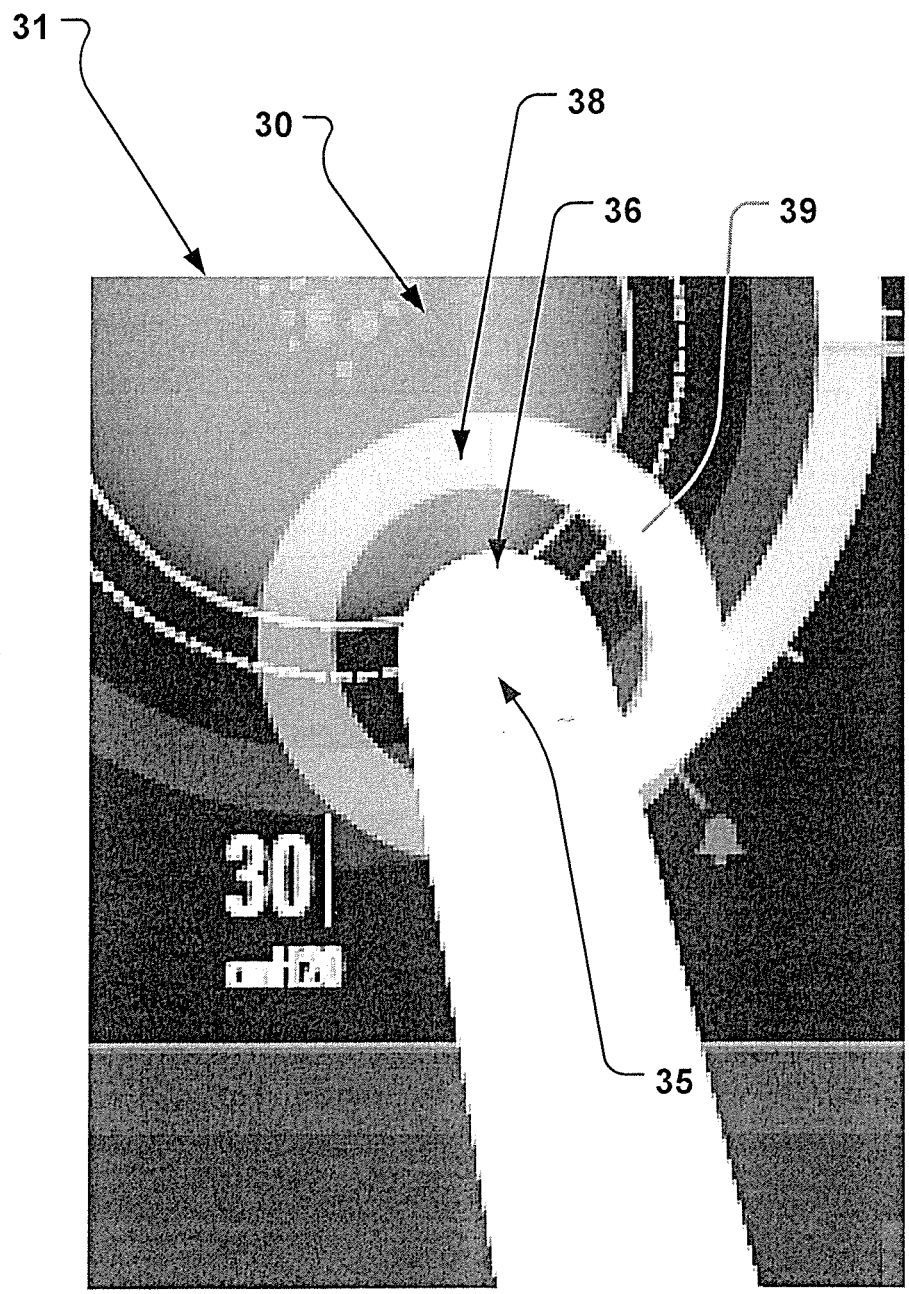
FIG. 4C is an enlarged view of a portion of FIG. 4A.

FIG. 4C is an enlarged view of a portion of FIG. 4A at the location where a finger tip 36 touches the touch screen for the gesture 35.

A visual feedback is provided to the user that the tap is recognized as a feedback indicator 38 is displayed to the operator. In the example, the feedback indicator 38 is illustrated as a full circle. The indicator 38 may have other shapes, such as a curved or straight bar, an hourglass, etc. A specific example would be a progress bar. The progress bar may be displayed at the first screen area 31. A progress bar is a straight bar of defined length, where a bar fills along the length with the hold time until the threshold time is reached and the second content 40 is accessed. The indicator 38 has an extension for illustrating the entire time length that has to lapse before an action is performed at a predefined time threshold, here the transition to the second content 40. An animated portion 39 indicates the time that has currently lapsed. The animated portion may for instance be a curved or straight bar portion in a different grey shade or color than the remaining portion of the indicator 38. The user can thus both realize that the time towards a threshold time is lapsing and how large portion relative the entire time to the threshold time has lapsed respectively remains to reaching the threshold time.

The threshold time may be pre-defined and stored in a memory. It may be dependent on the first content 30. Alternatively, or in addition, it may be dependent on the second content 40. In some examples of the disclosure the method includes providing user access to safety critical functions when the threshold time is exceeded. The more safety critical the second content is, e.g. adjustments that may be accessed and made in the second content, the longer the time threshold may be.

In FIG. 4B, a second content 40 is illustrated. The operator has access to the second content 40.

The second content may be an operational mode of editing at least the first content. The GUI may comprise elements in the second content for adjusting operative parameters of the breathing apparatus, such as ventilation parameters, curves of ventilation parameters, or breathing modes. The second content may comprise soft buttons, icons or other input units.

In the example illustrated in FIG. 4B, the second content is illustrated as such an edit mode. In the illustrated example of FIG. 4B, the second content includes portions of the first content that are selectable for adjustment by the operator. These portions may be indicated by frames around screen areas selectable, e.g. by a tap gesture, for adjustments or further information or action. These portions include for instance one or more fields for adjusting numerical values 41. The framed portions include for instance one or more icons 42, such as for accessing a help screen. The framed portions include for instance one or more fields 43, 46 for closing the edit mode, e.g. for returning to the first content. These portions include for instance one or more fields for adjusting scales of curves 44, or fields for adjustment of other curve related parameters 45, such as sweep speed or curve shape. One or more soft buttons 47 may be provided in the second content 40, see e.g. FIG. 6B.

A difference between the first content and the second content is that the operator intentionally, but intuitively, has requested the second content. Upon the operator's request, the operator has its attention on the second content and elements like soft buttons 47 are not perceived as confusing by the operator.

Figure 3:
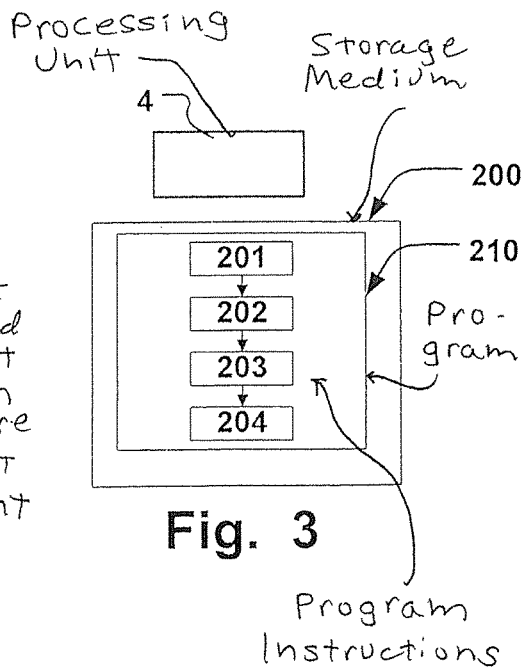
FIG. 3 is a schematic illustration of an example of a computer-readable medium.

FIG. 3 is a schematic illustration of an example of a computer-readable medium 200. The computer-readable medium 200 has embodied thereon a computer program 210 is disclosed for processing by one or more processing units, in particular a processing unit 4 of a breathing system. The computer-readable storage medium 200 has for this purpose instructions stored thereon that when executed by the processing unit 4 perform operations for providing user communication via a touch screen of the breathing system 1 including a breathing apparatus 2. The instructions include displaying 201 at least a first content at a first screen location of the touch screen; detecting 202 a user input comprising a gesture of one or more gestures at the first screen location; selecting 203 a second content, different from the first content and different for each gesture, in dependence of the gesture and the first content; and providing 204 the second content on the touch screen.

FIGS. 5A, 5B, 6A, 6B, 7A, 7B, 8A, 8B, 9A, 9B, 10A, 10B, 11A, and 11B are schematic illustrations of various examples of portions of GUIs of a display of a breathing system with a first content 30 and a second content 40 provided upon user interaction including a gesture on said first content, respectively.

Figure 5A:
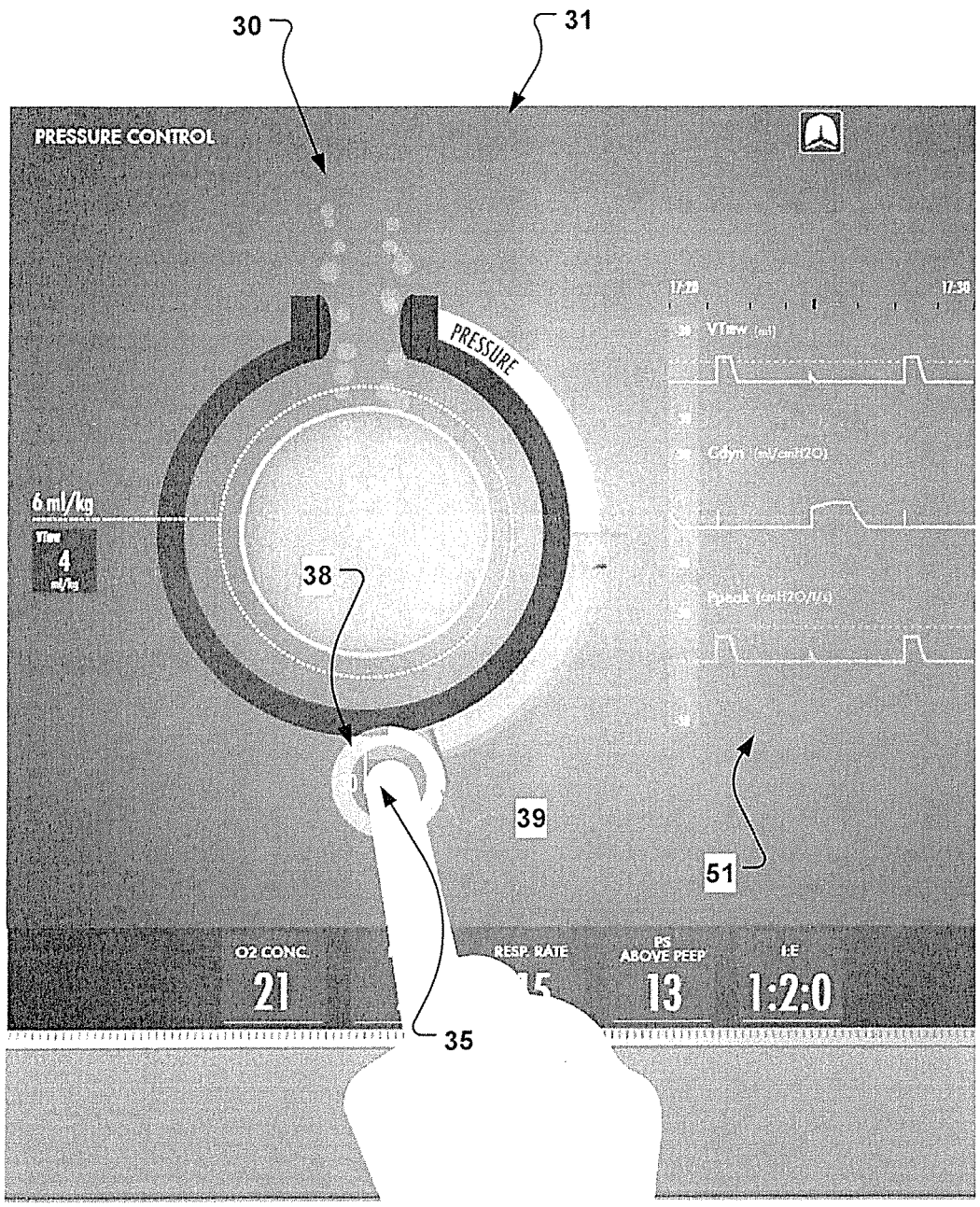

In FIG. 5A, a first content 30 is illustrated. The first content 30 illustrated in the example of FIG. 5A includes a ventilation strategy indicator in a screen view different than that illustrated in FIG. 4A. Similar to the illustration of FIG. 4A, a tap and hold gesture 35 is illustrated in FIG. 5A. A trend element 51 includes curves for one or more ventilatory parameters over a selectable time length longer than a few breathing cycles (which in contrast are displayed as real time curves 60). In the first content 30, the time length is 10 minutes, namely a between illustrated in the example between 17.20 to 17.30.

As in the example of FIGS. 4A-4C, the input is intuitively associated with a second content with a user input that is tolerant as to the exact screen location of the input.

Figure 5B:
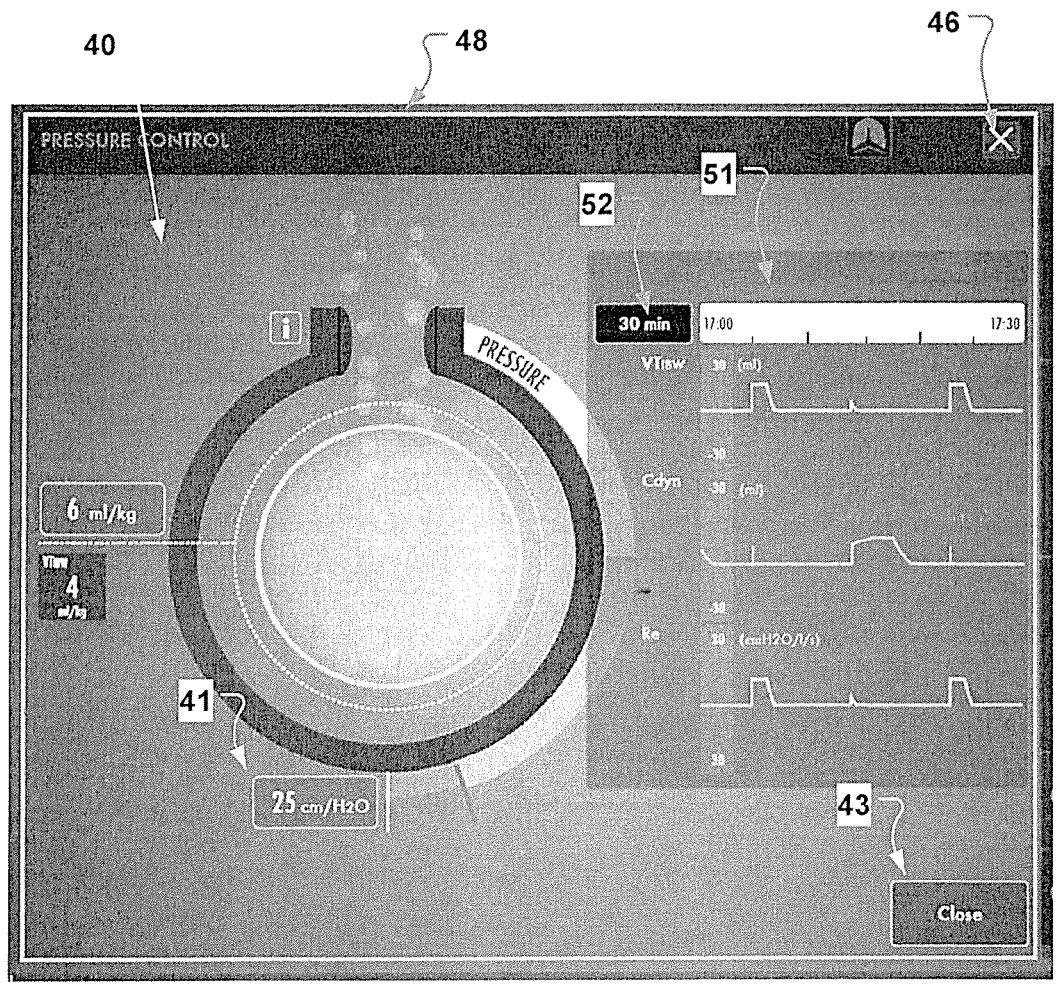

In FIG. 5B, a second content 40 is illustrated upon access from the first content 30 illustrated in FIG. 5A.

A button 52 is provided to select a different time length for the trend 51 element. Upon selecting button 52, the user may change the setting by suitable elements, like sliders, +/− or up/down buttons, or a numerical field where a number is selectable. Upon confirmation, the updated value is transferred to the second content. In the example of FIG. 6B, the selectable time length of the trend element 51 is changed to 30 minutes from the initial 10 minutes interval illustrated in FIG. 6A. The same time length is in the example selected for the plurality of trend curves. In other examples, individual time lengths may be selected (not shown) for one or more of a plurality of trend curves.

Figure 6A:
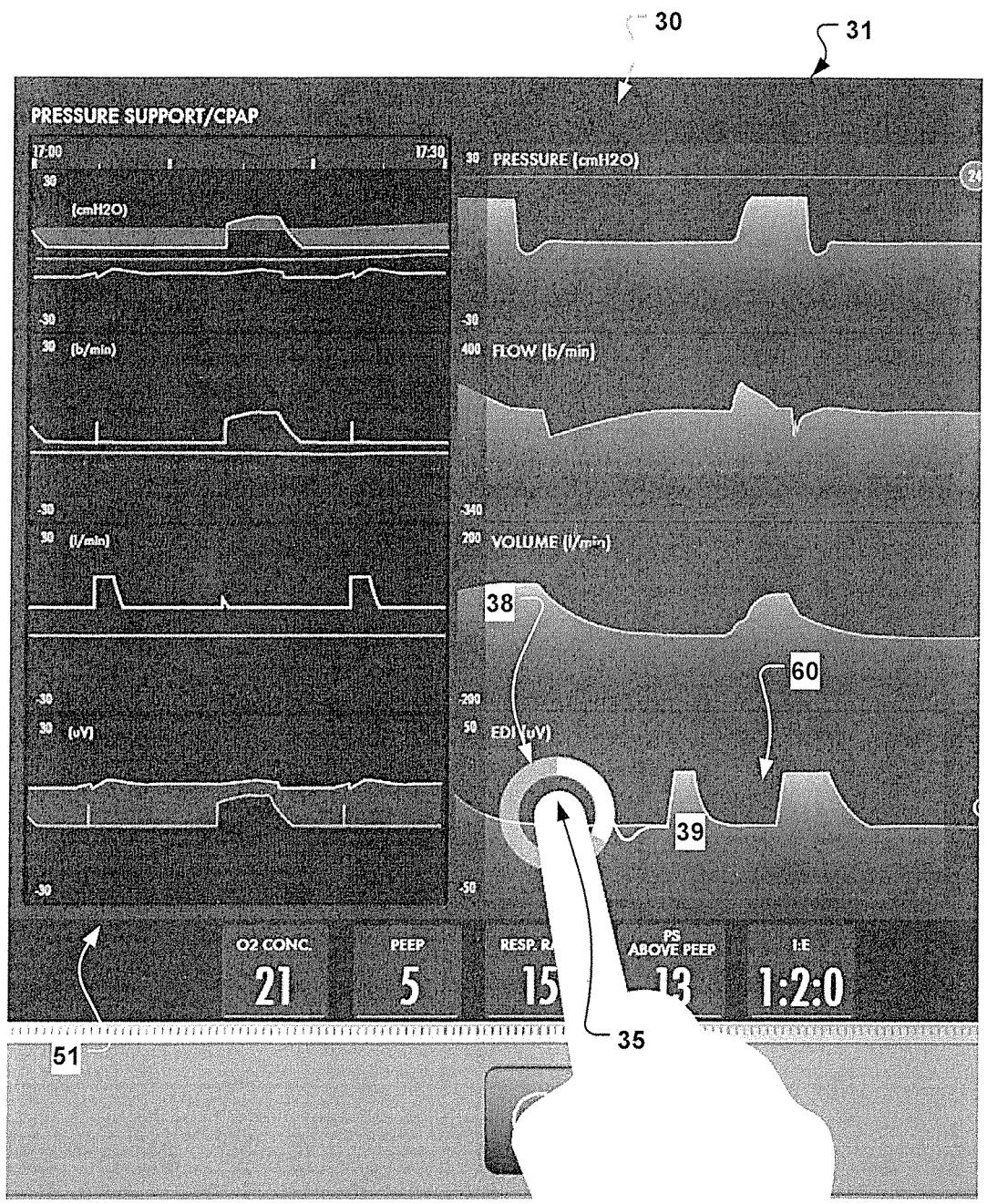
Figure 6B:
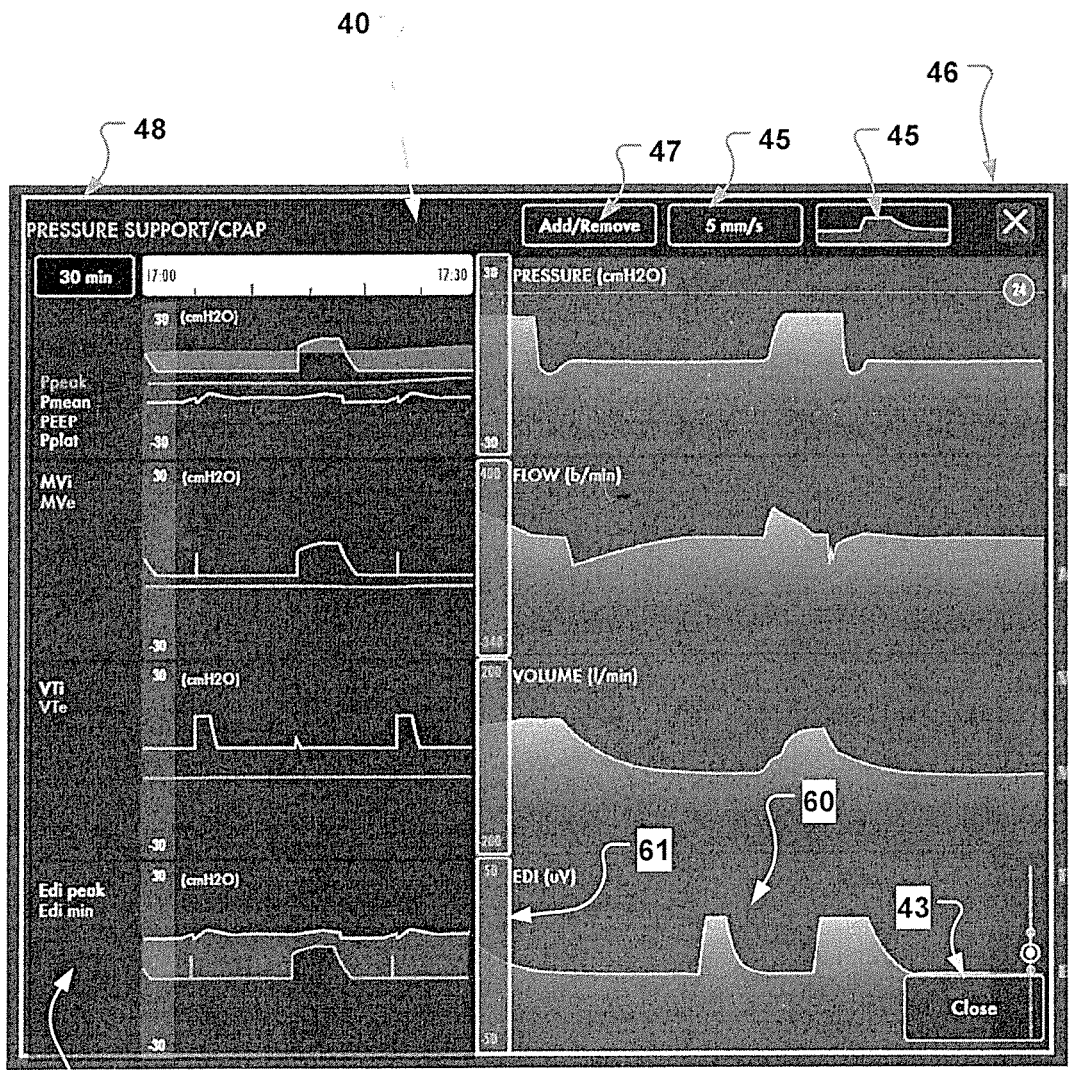

In FIG. 6A, a first content 30 is illustrated. In the present example, the first content 30 includes a curve 60. As in the previous examples, the input is intuitively associated with a second content with a user input that is tolerant as to the exact screen location of the input. In the present example, user input may be accepted anywhere on the line of the curve, or adjacent to it.

In FIG. 6B, a second content 40 is illustrated upon access from the first content 30 illustrated in FIG. 6A. The second content is an edit mode for adjusting view settings of the first content which is accessed upon a tap and hold gesture as described above. For instance, a range 61 of a curve 60 is selectable for adjustment, e.g. via a +/− input element or similar (not shown) when selected. One or more soft buttons 47 are provided in the second content 40 in the example illustrated in FIG. 6B. The soft button illustrated in the example is an Add/Remove button for adding or removing certain curves included in the GUI.

Figure 7A:
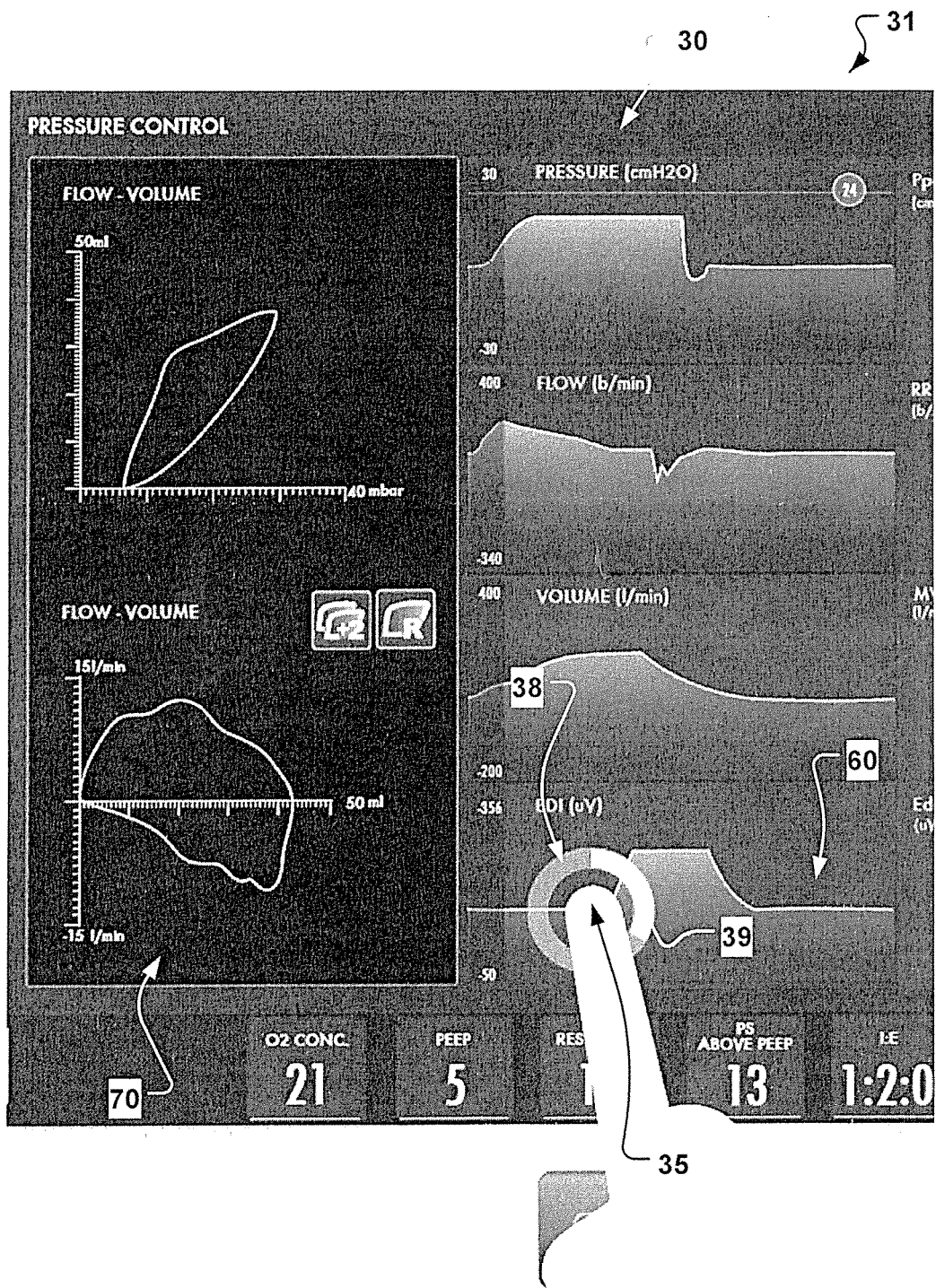

In FIG. 7A, a first content 30 is illustrated. In the present example, the first content 30 includes a curve 60 and loops 70. As in the previous examples, the input is intuitively associated with a second content with a user input that is tolerant as to the exact screen location of the input.

Figure 7B:
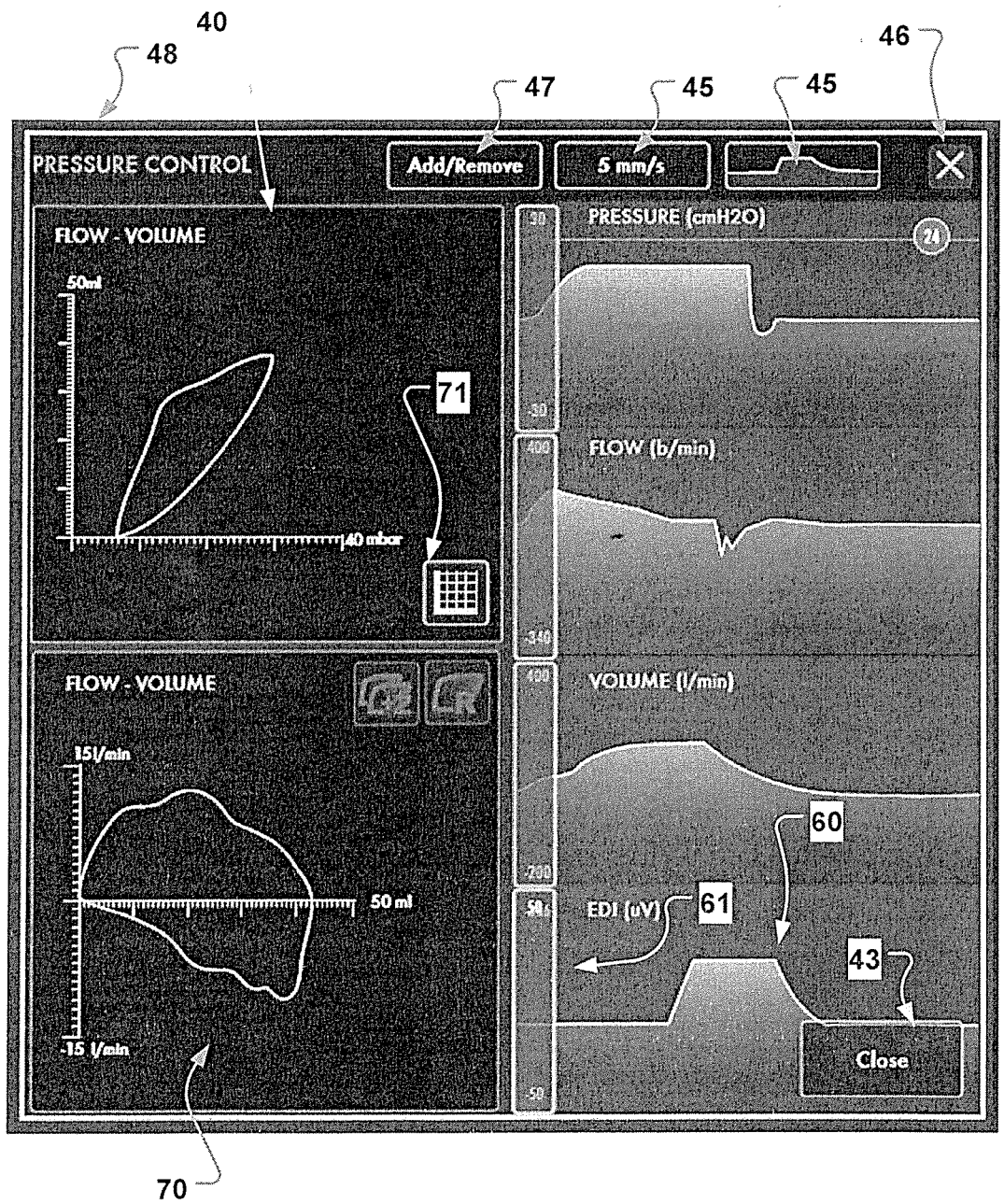

In FIG. 7B, a second content 40 is illustrated upon access from the first content 30 illustrated in FIG. 7A. The second content is an edit mode for adjusting view settings of the first content which is accessed upon a tap and hold gesture as described above. The edit mode is in the example for editing of curves 60 and loops 70. For instance a range 61 of a curve 60 is selectable for adjustment. One or more soft buttons 47 are provided in the second content 40 as in the example illustrated in FIG. 6B. A button 71 or similar input element may be provided for editing view settings for one or more of the loops 70.

Figure 8A:
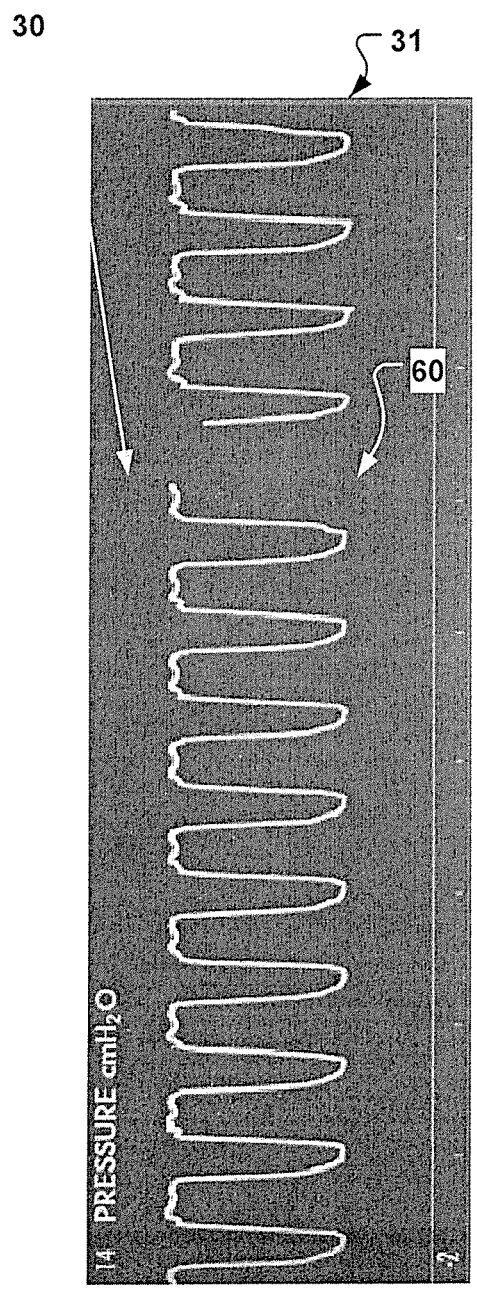

In FIG. 8A, a first content 30 is illustrated. In the present example, the first content 30 includes a curve 60. As in the previous examples, the input is intuitively associated with a second content with a user input that is tolerant as to the exact screen location of the input. The second content is here accessed via a tap gesture.

Figure 8B:
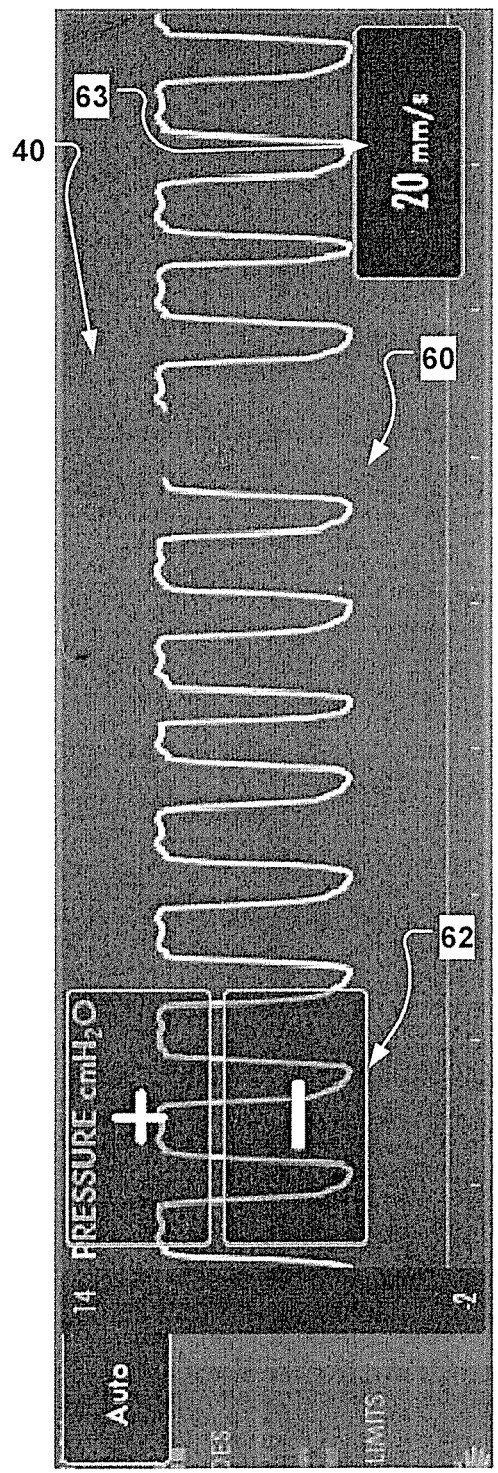

In FIG. 8B, a second content 40 is illustrated upon access from the first content 30 illustrated in FIG. 8A. The second content is an edit mode for adjusting the sweep speed of the curve 60. A button 63 is provided to illustrate the current sweep speed. It may be selected by the operator, e.g. by a tap gesture, to change the current sweep speed to another value. Alternatively, or in addition, adjustment elements 63 may be provided to change the sweep speed. Suitable elements are for instance sliders, +/− buttons (as shown), up/down buttons, etc.

Figure 9A:
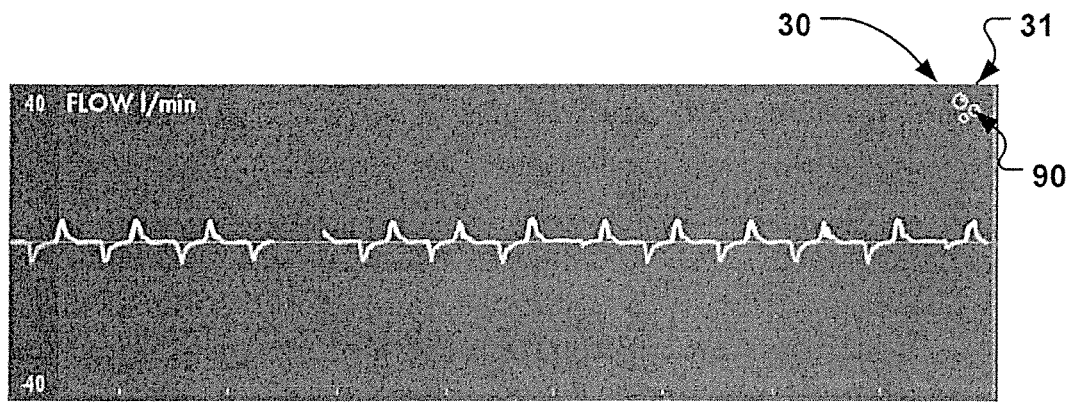

In FIG. 9A, a first content 30 is illustrated. In the present example, the first content 30 includes a symbol 90, here illustrated as bubbles. A symbol 90 has no contour line defining a certain screen area related to the symbol. A symbol 90 should thus not be confused with an icon.

By tapping at or on the symbol 90, the second content is selected for display on the touch screen. As in the previous examples, the input is intuitively associated with a second content with a user input that is tolerant as to the exact screen location of the input.

Figure 9B:
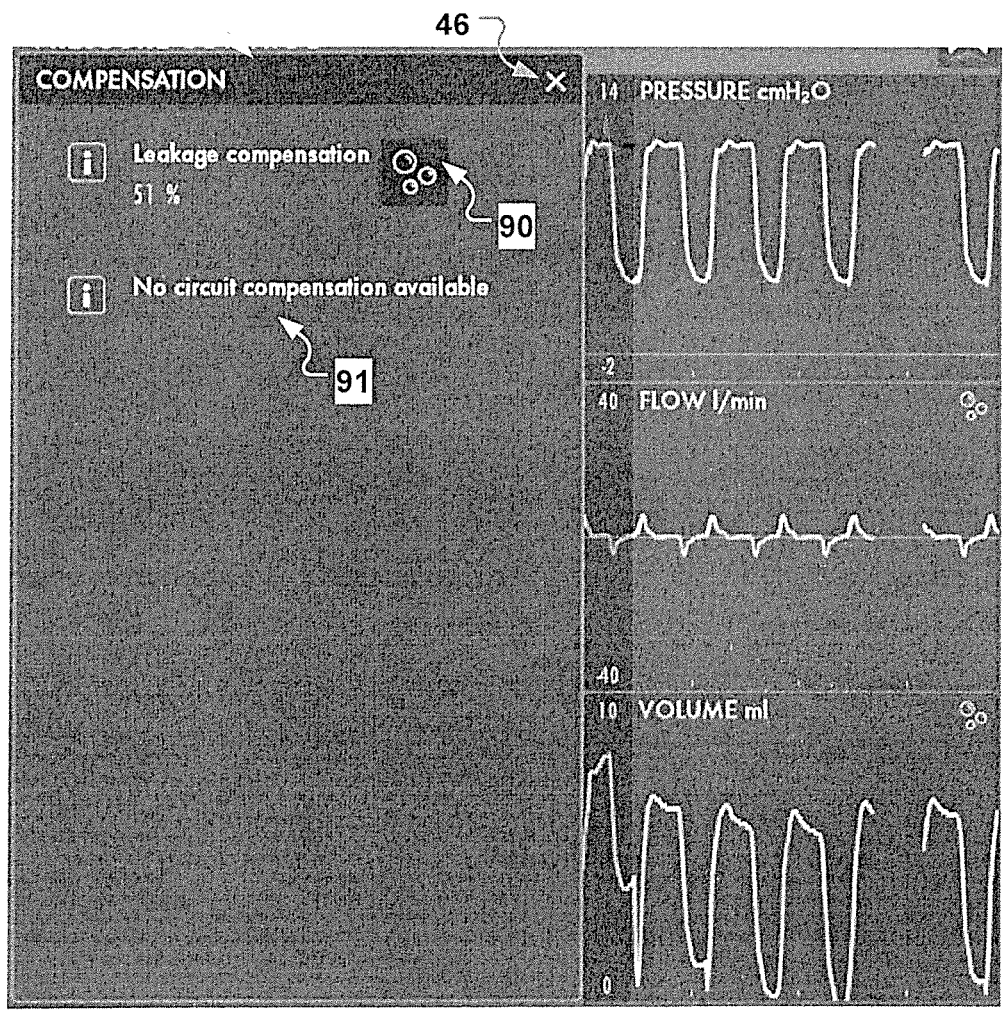

In FIG. 9B, a second content 40 is illustrated upon access from the first content 30 illustrated in FIG. 9A. Information elements 91 related to symbol 90, e.g. a mode where a certain function related to the symbol 90 can be activated or deactivated, are provided in the second content 40.

The symbol 90 illustrated in the example and shown in the Figures as bubbles may be related to a leakage compensation of the breathing circuit in the breathing system 1. This is also understood from the illustration in FIG. 9B. The bubbles symbol does not give an explicit, direct information that adjustments to leakage compensation is related to the bubbles symbol when user input via a specific gesture is made at the symbol to get access to the second content 40.

Other examples of symbols may include other abstract symbols than the specific bubbles symbol described above. For instance examples include a symbol for a catheter, or a symbol for electrodes, or a symbol for a catheter with electrodes. For instance, the symbol may be shown in a first screen area 31 related to a Neurally Adjusted Ventilatory Assist (NAVA) mode of ventilation, which is a mode of ventilation that delivers ventilatory assist in proportion to and in synchrony with the patient's Edi signal, i.e. the electrical activity of the diaphragm. Edi is for instance measured using an esophageal measurement catheter. For instance upon a pre-defined gesture (such as a Tap an hold with a hold portion time threshold) on a symbol for a catheter with electrodes, or a curve of an Edi signal, or a metric for an Edi signal measure, the second content 40 may be entered. The second content may pertain to positioning of the catheter, selection of electrodes, measurement maneuvers, related to the NAVA mode. Apart from the diphragmal EMG (Edi), other examples for symbols include symbols for other respiratory bioelectric signals and muscular signals in synchrony with breathing, etc.

Figure 10A:
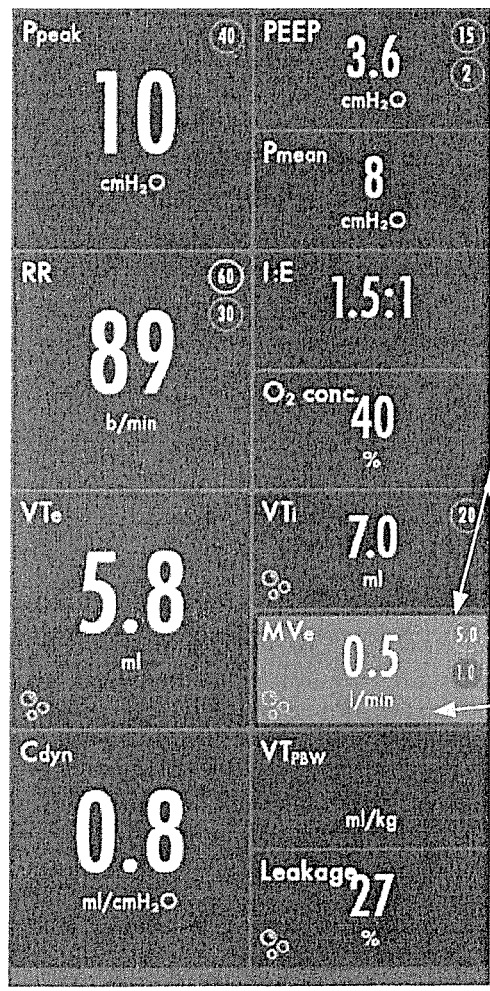

In FIG. 10A, an example of a first content 30 is illustrated. In the present example, the first content 30 includes a metric field 80 for a specific ventilation parameter. The metric field 80 is in the example in an alarm situation, e.g. having an alerting background color, and/or flashing, etc. to notify an operator of the alarm situation. As in the previous examples, the input is intuitively associated with a second content with a user input that is tolerant as to the exact screen location of the input at the metric field 80.

Figure 10B:
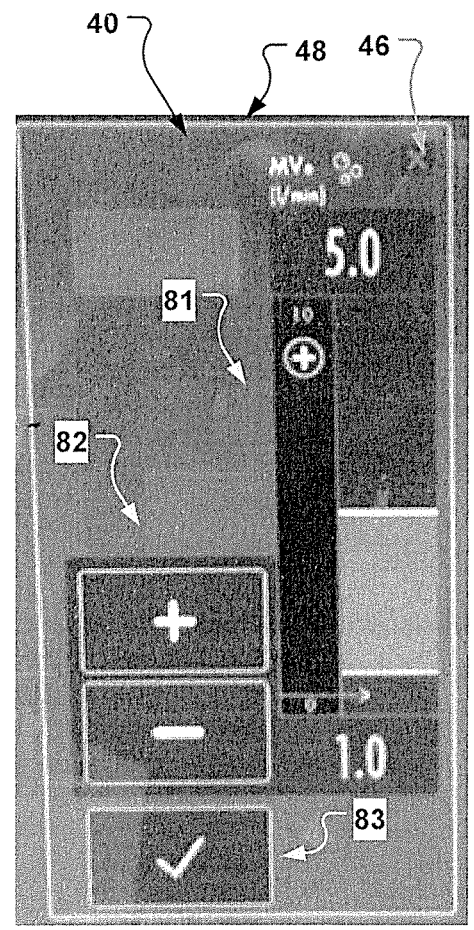

In FIG. 10B, a second content 40 is illustrated upon access from the first content 30 illustrated in FIG. 10A. The second content 40 includes adjustment elements for the alarm limits for that specific ventilation parameter of the metric field 80. Such adjustment elements may include a sliding bar 81 for adjusting lower and/or upper alarm limits. Moreover, sliders, +/− buttons 82, up/down buttons, etc. may be provided. A confirm button 83 provides for accepting the adjustments made via the adjustment elements.

Figure 11A:
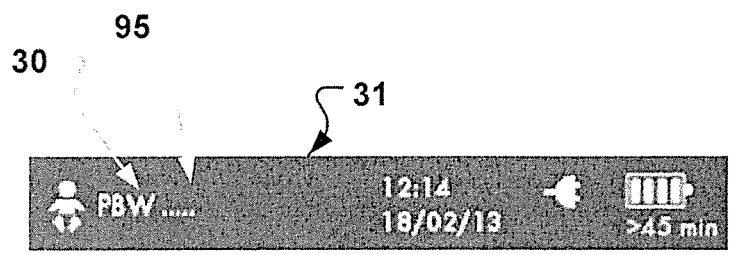

In FIG. 11A, an example of a first content 30 is illustrated. In the present example, the first content 30 includes a status field 95. The status field 95 may comprise fields for example for patent data, patient type indicator, date, battery charge status, etc. As in the previous examples, the input is intuitively associated with a second content with a user input that is tolerant as to the exact screen location of the input at the status field 95.

Figure 11B:
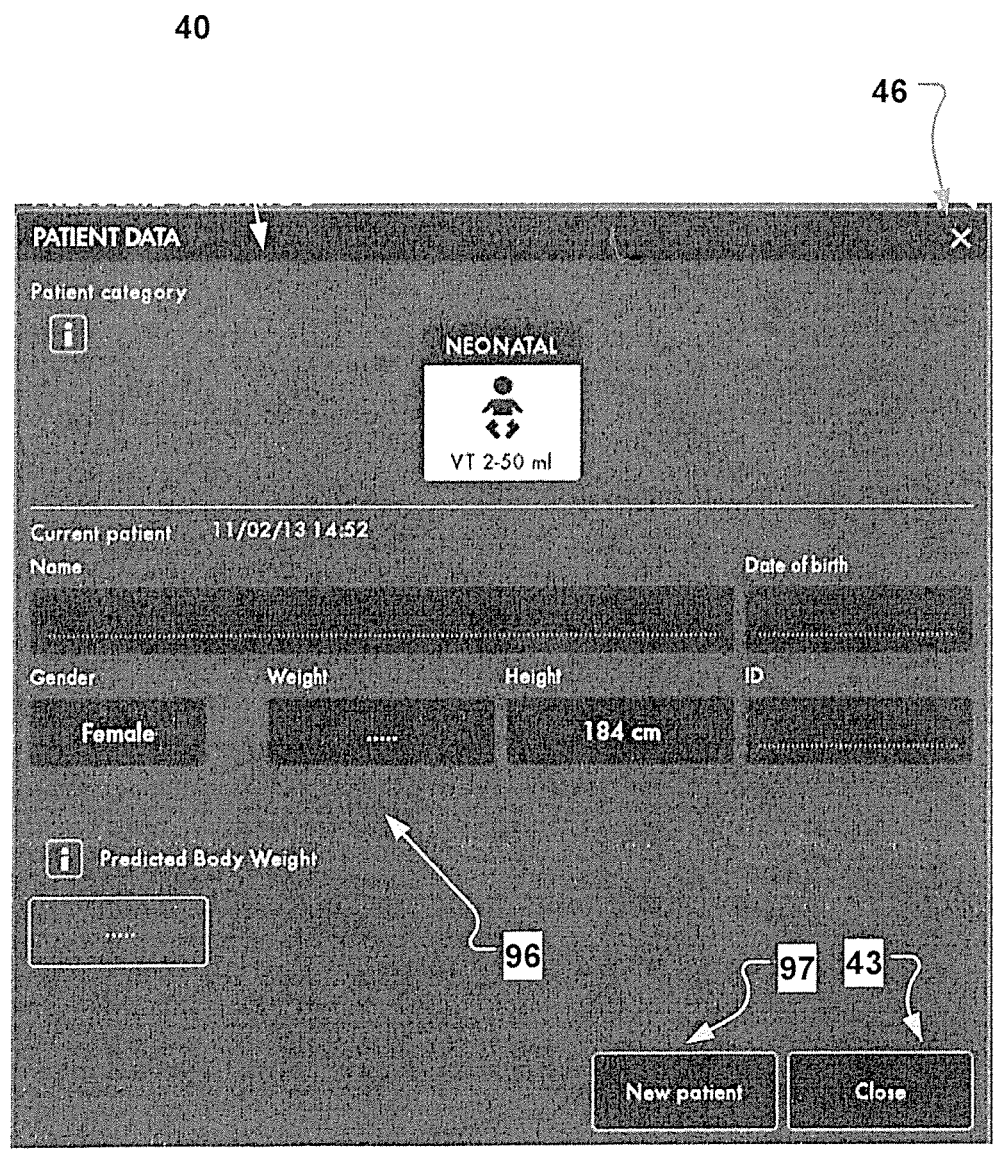

In FIG. 11B, a second content 40 is illustrated upon access from the first content 30 illustrated in FIG. 11A. An edit field 96 for entering or adjusting patient data is provided. For selecting that a new patient is ventilated and old patient data is deleted, a New patient button 97 is provided.

As illustrated in the examples, the second content 40 may be provided at least partly overlayed to or adjacent to the first content 30.

The second content 40 may comprise at least a portion of the first content 30. It may in addition include a frame 48 around an area containing the second content, see e.g. FIGS. 4B, 5B, 6B, 7B, and 10B. The frame 48 facilitates for the operator to identify that a different operational mode of the breathing apparatus is entered from the first content. The frame 48 further assists in delimiting the second content 40 from remaining screen portions, thus keeping different portions of the GUI apart.

The first screen location 31 where the first content is displayed may be a sub-area of the touch screen's total display area. The sub area may be a display area where loops and/or waveforms are displayed. The sub area may alternatively or in addition include one or more metrics fields.

In a particular example, the first screen location 31 may include the touch screen's total display area. In this particular example, it is sufficient to perform the gesture 35 on any portion of the screen to access the second content 40. Again, it is dependent on the first content 30 on the touch screen. For instance, the first content 30 may be a so-called "family view" comprises background images that cover a large portion of the display area. This is in detail described in PCT/EP2012/061901. Operational parameters and metrics are displayed in the same family view, but in a limited number compared to a clinical expert view. Ventilation continues unchanged during the family view, and is in particular advantageous when non-clinical persons are at the breathing apparatus as it is less stressful than a clinical view that in contrast is only showing metrics, parameter curves, and other clinical details that secondary users do not fully understand.

When a clinical operator wants to quickly switch from a specific view like the family view to another view, like the clinical expert view, the operator may do so by simply tapping on the touch screen in the family view (or similar). The GUI will then change views directly and immediately, e.g. from the family view to the clinical expert view. In the clinical expert view, multiple first contents 30 are displayed, which each lead to gesture dependent different second contents as for instance elucidated in the above examples, like curves, metric fields, ventilation strategy indicator elements, etc.

The second content 40 may comprise an icon and/or a soft button to return to the first content 30, such as the button 46 or the button 43.

Another example is that the first content 30 that is displayed, and which is leading to gesture dependent different second content, includes any of the above examples, like curves, metric fields, ventilation strategy indicator elements, etc. Touching a specific first screen location 31 of that first content 30 may lead to a preview mode for switching to a different screen view or layout of the GUI. The processing unit 4 is then configured to control the display 3 such that on a display area thereof the second content is provided in form of a preview of the second screen view or a second operational mode—before the actual switching, i.e. activation of the second operational mode from within the second content 40. Such a preview is described in PCT/EP2012/061901, such as shown in FIG. 8 thereof, or in PCT/EP2013/054180 of the same applicant as the present application and which is incorporated herein by reference for all purposes. The preview mode, may be entered by a Tap and Hold gesture of a predefined time length of the hold portion. In the second content 40 an Accept step may be performed on the touch screen to switch to the second view being previewed in the second content 40.

The first content may include a metric of a ventilatory parameter, such as an oxygen content metrics, such as an inspiratory oxygen content value delivered to the patient during ventilation. Upon a gesture like Tap and hold, a function or a change in ventilatory parameters may be obtained, at least temporary. For instance upon a gesture like a Tap and hold on the oxygen content metrics, an oxygen boost function indicator (not shown) may be provided as a second content. The oxygen boost function is giving access to an oxygen flush with adjustable O2% value. In the second content the O2% value may be selected via suitable input elements. Alternatively, or in addition, an oxygen boost may directly be given to the patient, e.g. during a limited number of breaths, when the second content is accessed. Other functions of the ventilator may be accessed in this manner and directly executed after a certain hold time threshold is exceeded. The second content 40 allows for instance to quickly abort the directly accessed and executed function of the ventilator. Other examples than O2 boosts are temporary increased PEEP levels, ventilation pauses, temporary increased breath frequency, etc. in dependence of the first content 30 e.g. being a PEEP metric, a pause portion of a patient gas flow curve, a respiratory rate metric, respectively.

A further example is access to ventilation mode related adjustments. For instance a gesture made on or at a specific symbol, e.g. the symbol on the right on the top of FIG. 5A, which preferably does not lead, suggest or associate the second content. Alternatively, or in addition, a gesture may be made on or at a text or abbreviation of a current ventilation may be performed, e.g. the text on the left on the top of FIG. 5A. The text is not an icon or a menu selection rather than a status description which conventionally does not allow for any user input. Alternatively, the gesture may be made on a field having no context in the close vicinity, like a single colored background, e.g. a black or blue background during a ventilation mode, e.g. the screen area between the top and middle left illustrated in FIG. 5A. Different gestures may lead to different second context. For instance a Tap at such a first screen location may lead to a status indication window of the breathing apparatus in a current ventilation mode. A Tap and hold at the same first screen relation may lead to access of a control mode for adjusting settings of the current ventilation mode. Alternatively, or in addition, a different ventilation mode may be selected in the related second content (not shown).

The symbol may also be a control indicator for accessing safety critical functions of the breathing apparatus, such as for stopping an on-going ventilation.

The present invention has been described above with reference to specific embodiments. However, other embodiments than the above described are equally possible within the scope of the invention. Different method steps than those described above, performing the method by hardware or software, may be provided within the scope of the invention.

The different features and steps of the invention may be combined in other combinations than those described. The scope of the invention is only limited by the appended patent claims.

I claim:

1. A breathing system for ventilating a patient, the breathing system comprising:
    a breathing apparatus adapted for connection to a patient to implement ventilation of the patient, a touch screen for interaction of a user with the breathing apparatus, and a processing unit operatively connected to the touch screen, wherein the processing unit is configured to
        define a sub-area of the touchscreen as a first screen location that is capable of displaying a first content, wherein the first screen location and the first content are free of an indication of a second content and are also free of any soft buttons and menus;
        display at least the first content at the first screen location of the touch screen, wherein the first content is at least one of an indicator, curve, metric symbol or a parameter related to ventilation of the patient;
        receive a user input that includes a touch by a single finger made on the touch screen anywhere within or adjacent to the first screen location and without activating a soft button on the touch screen, wherein the input occurs on the first content and causes a window to open that comprises the second content; and
        display the second content on the touch screen at a screen location that partly includes the first screen location or that is remote from the first screen location.

2. The system of claim 1, wherein said touch is a tap and hold gesture, and wherein said processing unit is configured to provide said second content upon a hold time portion of said tap and hold gesture exceeding a threshold of pre-defined time length.

3. The system of claim 2, wherein said threshold is dependent on said first content.

4. The system of claim 2, wherein said processing unit is configured to provide a visual feedback to said user during said hold portion illustrating elapsed hold time and time until said threshold is reached.

5. The system of claim 4, wherein said processing unit is configured to provide user access to safety critical functions when said threshold is exceeded.

6. The system of claim 1, wherein said processing unit is configured to provide said second content upon confirmation to display the second content by said user.

7. The system of claim 1, wherein said first content is at least one item selected from the group consisting of:
    a ventilation strategy indicator;
    a curve of a ventilation parameter;
    a metric of a ventilation parameter in normal operation;
    a metric of a ventilation parameter when an alarm limit thereof is passed; and
    a bubbles symbol.

8. The system of claim 1, wherein said second content is at least one item selected from the group consisting of:
    a graphical interface for adjusting operative parameters of said breathing apparatus comprising curves of ventilation parameters;
    short trend curves for at least one ventilation parameter;
    a graphical interface for adjustment of alarm limits; and
    at least one graphical loops of one or more ventilation parameters.

9. The system of claim 1, wherein said gesture, said first content and said second content are selected from the group consisting of:
    a tap, a metric or curve during an alarm, alarm adjustments;
    a tap and hold, a curve, a configuration mode for said curve.

10. The system of claim 1, wherein said first content is also free of any icons providing an indication of said second content.

11. The system of claim 10 wherein said touch constitutes a tap and hold gesture, and wherein said processing unit is configured to provide said second content upon a hold time portion of said tap and hold gesture exceeding a threshold of predefined time length.

12. A method of internally controlling a breathing apparatus adapted for connection to a patient to implement ventilation of the patient, said breathing apparatus having a processor in communication with a touch screen for interaction of a user with said breathing apparatus, said method comprising the steps of:
    in the processor, defining a sub-area of the touch screen as a first screen location;
    displaying at least a first content at the first screen location of the touch screen, wherein the first content is at least one of an indicator, curve, metric symbol or a parameter related to ventilation of the patient, and wherein the first screen location and the first content are free of an indication of a second content and are also free of any soft buttons and menus;
    receiving a user input comprising a touch provided by a single finger made anywhere on the touch screen that is within or adjacent to the first screen location;
    selecting theft second content related to the first content in dependence of the gesture and the first content;
    displaying the second content on the touch screen; and wherein the user input is received without pressing a soft button on the touch screen.

13. The method of claim 12, wherein said touch is a tap and hold gesture, and providing said second content upon a hold time portion of said tap and hold gesture exceeding a threshold of pre-defined time length, and optionally providing a visual feedback to said user during said hold portion illustrating elapsed hold time and time until said threshold is reached, and wherein said threshold preferably is dependent on said first content.

14. The method of claim 13, comprising providing user access to safety critical functions when said threshold is exceeded.

15. A non-transitory computer-readable storage medium having instructions stored thereon that, when executed by at least one processor of a breathing system, cause the breathing system to perform operations for providing user communication via a touch screen of the breathing system that includes a breathing apparatus adapted for connection to a patient to implement ventilation of the patient, wherein the instructions cause the at least one processor to operate the breathing system so as to:
    display at least a first content at a first screen location of the touch screen, wherein the first content is at least one of an indicator, curve, metric symbol or a parameter related to ventilation of the patient, and wherein the first screen location and the first content are free of an indication of a second content and are also free of any soft buttons and menus;

detect a user input comprising a touch provided by a single finger made anywhere within or adjacent to the first screen location and without pressing a soft button on the touch screen;

select the second content related to the first content in dependence of the gesture and the first content;

display the second content on the touch screen.

16. A breathing system for ventilating a patient, the breathing system comprising:
   a breathing apparatus adapted for connection to a patient to implement ventilation of the patient;
   a touch screen for interaction of a user with the breathing apparatus; and
   a processing unit of the breathing apparatus that is operatively connected to the touch screen;
   wherein the processing unit is configured to
      define a sub-area of the touchscreen as a first screen location;
      display at least a first content at the first screen location of the touch screen, wherein the first content is at least one of an indicator, a curve, or a metric symbol related to ventilation of the patient;
      receive a user input comprising one or more gestures provided by a single finger that are made at the first screen location of the touch screen and without activating a soft button;
      display a second content upon receipt of the user input, with the second content displayed by user input made at the first content of the first screen location and the second content is displayed by user input made adjacent the first content of the first screen location;
      wherein the second content is displayed on the touch screen at a screen location that at least partly includes the first screen location; and
      the first content is free of an indication of any second content and wherein at least the first screen location is soft-button less.

17. The system of claim 16, wherein said one or more gestures is a tap and a hold gesture.

18. The system of claim 16, wherein an area adjacent said touch screen is free of buttons that are associated with said first content.

19. The system of claim 16, wherein said processing unit is configured to provide said second content upon confirmation to display the second content by said user.

20. The system of claim 16, wherein said first content is at least one item selected from the group consisting of:
   a ventilation strategy indicator;
   a curve of a ventilation parameter;
   a metric of a ventilation parameter in normal operation;
   a metric of a ventilation parameter when an alarm limit thereof is passed; and
   a bubbles symbol.

21. The system of claim 16, wherein said second content is at least one item selected from the group consisting of:
   a graphical interface for adjusting operative parameters of said breathing apparatus comprising curves of ventilation parameters;
   short trend curves for at least one ventilation parameter;
   a graphical interface for adjustment of alarm limits; and
   at least one graphical loops of one or more ventilation parameters.

22. A breathing system for ventilating a patient, the breathing system comprising:
   a breathing apparatus adapted for connection to a patient to implement ventilation of the patient;
   a touch screen for interaction of a user with the breathing apparatus; and
   a processing unit that is operatively connected to the touch screen;
   wherein the processing unit is configured to
      define a sub-area of the touch screen as a first screen location, wherein at least the first screen location is soft-button less;
      display at least a first content at the first screen location of the touch screen, wherein the first content is at least one of an indicator, curve, metric symbol or a parameter related to ventilation;
      receive a user input comprising a gesture provided by a single finger made at the first screen location;
      select a second content related to the first content in dependence of the gesture and the first content;
      display the second content on the touch screen at a screen location that at least partly includes the first screen location; and
      wherein the first content is free of any icons, soft buttons or menus providing an indication of the second content and the user input is received without activating any soft button on the touch screen.

23. A breathing system for ventilating a patient, the breathing system comprising:
   a breathing apparatus adapted for connection to a patient to implement ventilation of the patient;
   a touch screen for interaction of a user with the breathing apparatus; and
   a processing unit operatively connected to the touch screen, wherein the processing unit is configured to
      define a sub-area of the touchscreen as a first screen location capable of displaying a first content, wherein the first screen location is free of indication of a second content, wherein at least the first screen location is soft-button less, and wherein the second content is substantially different from the first content;
      display at least the first content at the first screen location of the touch screen, wherein the first content is at least one of an indicator, curve, metric symbol or a parameter related to ventilation of the patient;
      receive a user input that includes a touch and a gesture provided by a single finger made on the touch screen within or adjacent to the first screen location and without activating a soft button on the touch screen;
      select a second content related to the first content in dependence of the gesture made on the touch screen and on the first content; and
      display the second content on the touch screen at a screen location that either partly includes the first screen location or that is remote from the first screen location;
      wherein when the gesture is a first gesture made on the touch screen the second content selected is of one type and when a second gesture is made on the touch screen the second content selected is of a substantially different type than selected when the gesture is the first gesture.

24. A breathing system for ventilating a patient, the breathing system comprising:
   a breathing apparatus adapted for connection to a patient to implement ventilation of the patient;
   a touch screen for interaction of a user with the breathing apparatus; and
   a processing unit operatively connected to the touch screen, wherein the processing unit is configured to define a sub-area of the touch screen as a first screen location capable of displaying a first content, wherein the first screen location and the first content are free of an indication of a second content that is associated with the first content and are also free of any soft buttons and menus;

display at least the first content at the first screen location of the touch screen, wherein the first content is at least one of an indicator, curve, metric symbol or a parameter related to ventilation of the patient;

receive a user input comprising a tap and hold gesture made on the touch screen by a single finger anywhere within or adjacent to the first screen location, wherein the tap and hold gesture made on the touch screen is made without activating any soft button on the touch screen;

select the second content related to the first content in dependence of the tap and hold gesture made on the touch screen and on the first content; and display the selected second content on the touch screen, wherein the processing unit is configured to provide the second content upon a hold time portion of the tap and hold gesture exceeding a threshold of pre-defined time length.

* * * * *